United States Patent [19]

Smith

[11] Patent Number: 4,902,678

[45] Date of Patent: Feb. 20, 1990

[54] ANTI-VIRAL COMPOSITIONS

[75] Inventor: Kendall O. Smith, San Antonio, Tex.

[73] Assignee: Syntex (U.S.A.) Inc., Palo Alto, Calif.

[21] Appl. No.: 175,643

[22] Filed: Apr. 5, 1988

Related U.S. Application Data

[63] Continuation of Ser. No. 892,750, Jul. 29, 1986, abandoned, which is a continuation of Ser. No. 780,727, Sep. 27, 1985, abandoned, which is a continuation of Ser. No. 544,835, filed as PCT US82/00182 on Feb. 12, 1982, Published as WO83/02723 on Aug. 18, 1983, abandoned.

[51] Int. Cl.$^4$ .............. A61K 31/70; A61K 31/66; A61K 31/52
[52] U.S. Cl. ........................ 514/45; 514/50; 514/120; 514/262
[58] Field of Search .............. 514/262, 45, 50, 120

[56] References Cited

U.S. PATENT DOCUMENTS

| | | | |
|---|---|---|---|
| 3,767,795 | 10/1973 | Schleicher et al. | 424/212 |
| 4,215,113 | 7/1980 | Eriksson et al. | 424/212 |
| 4,347,360 | 8/1982 | Ogilvie | 424/251 |
| 4,355,032 | 10/1982 | Verheyden et al. | 424/253 |

OTHER PUBLICATIONS

Chemical Abstracts 91:133836c (1979).
Skipkowitz et al., Applied Microbiology, vol. 26, pp. 264-267 (1973).

Primary Examiner—Jerome D. Goldberg

[57] ABSTRACT

Combinations of 9-[[2-hydroxy-1-(hydroxymethyl)-ethoxy]methyl]guanine and at least one other antivirally active drug such as phosphonoacetic acid and its salts, phosphonoformic acid and its salts, acycloguanosine, or a 5-(2-halogenovinyl)-2'-deoxyuridine show synergy in their activity against various herpes virus infections including HSV-1 and HSV-2.

11 Claims, No Drawings

ANTI-VIRAL COMPOSITIONS

This is a continuation of pending application Serial No. 892,750, filed July 29, 1986, now abaondoned; which is a continuation of Serial No. 780,727, filed Setp. 27, 1985, now abandoned; which is a continuation of Serial No. 544,835, filed as PCT US82/00182 on Feb. 12, 1982, published as WO83/02723 on Aug. 18, 1983, now abandoned; collectively incorporated herein by reference.

FIELD OF THE INVENTION

This invention relates to pharmaceutical compositions, and more particularly to pharmaceutical compositions useful for treatment of viral infections such as herpes infections in mammals.

BACKGROUND OF THE INVENTION

Herpes simplex virus (HSV) infections are widespread in human populations, and pose a particularly difficult health problem. Genital herpes poses a serious health threat to women, in particular. Pregnant women with active genital herpes infections at the time of delivery have a 50-50 chance of passing it on to their babies. The American Academy of Pediatrics states that 60% of those babies born with HSV infections will die, and half of the survivors will suffer severe damage to the brain, nervous system and eyes ("Pediatrics" 66, 147-9, 1980). It has also been proposed that HSV2 may have a role in the onset of cervical cancer. There has been observed an association between sexual intercourse and cervical cancer, which may be explained by transmission of HSV-2.

Unlike other sexually transmitted diseases such as gonorrhea, syphilis and nongonococcal urethritis, there is currently no cure for herpes infections. Many of the drugs currently in clincial use may not be effective in reducing theseverity or the duration of the symptoms. Even after the symptoms disappear, herpes virus tends to remain dormant in nerve tissue, only to be reactivated at a later date to an active phase of infection, causing lesions ("cold sores") and other symptoms to recur. A drug can be considered effective if it diminshes the severity of the lesions, allows for more rapid healing, extends the period between recurrences of herpes infections or stops recurrences altogther.

Herpes simplex virus is one member of the family "Herpetoviridae"; other members of this family which infect humans are varicella-zoster, cytomegalovirus and Epstein-Barr virus. The family also includes varous members which attack animals. For example, there are three types of equine herpesvirus, a swine herpesvirus, a canine herpesvirus and a feline herpesvirus, among others.

As will all viruses, herpes virus invades healthy host cells on which it relies to provide its needs for replication. Herpes viruses (code for) some of the enzymes they need for replication, instead of relying completely on the host cell for all their needs. Hence, herpes viruses are subject to selective inhibition by certain drugs that interfere specifically with viral enzymes.

BRIEF REFERENCE TO THE PRIOR ART

A variety of drugs have been proposed and tested for treatment fo HSV infections. For example, U.S. Patent 4,199,574 Schaeffer, issued Apr. 22, 1980 discloses a wide variety of compounds said to be useful in such treatments, extensive testing of one of which (acycloguanosine or acyclovir, 9-[2-hydroxyethoxymethyl]-guanine) has been reported in the literature, with sometimes promising results. Another drug which has been explored is 5-iododeoxyuridine (IDU), but this has been reported to be effective only against herpes infections of the eyes. It also have undesirable side effects, associated with toxicity to normal cells. Adenine arabinoside (ara-A), phosphonoformic acid (PFA), phosphonoacetic acid (PAA), 2-deoxy-D-glucose (2DB), and 5-(2-halogenovinyl)-2'-deoxyuridines as exemplified by bromovinyl-deoxyuridine (BVDU) and its iodo-analog are other drugs which have some demonstrated activity against human herpesviruses.

U.S. Patent application serial No. 302,790 Kelvin K. Ogilvie, filed Sept. 16, 1981 discloses additional compounds having activity against herpes simplex viruses and showing promise of providing effective treatment of diseases caused by these viruses. The most promising of the drugs in the Ogilvie application is 9-[[(2-hydroxy-1-(hydroxymethyl)ethoxy]methyl]guanine, hereinafter sometimes referred to as G*.

SUMMARY OF THE INVENTION

It has now been found that therapeutic compositions having outstanding activity against herpes virus, whilst having no significant effect on normal host cells at antivirally effective dosage levels, can be prepared from combinations of G* and certain of the other compounds having a degree of anti-HSV activity of their own. In some cases the combinations are such more effective than one could have predicted from a consideration of the activitites of the compounds individually, indicating that some form of synergistic effect is taking place.

Thus, according to the present invention, there is provided a therapeutic composition having activity against herpes virus infections and comprising in combination 9-[[2-hydroxy-1-(hydroxymethyl)-ethoxy]methyl]guanine as a first active component, and a second active component selected from the groups consisting of phosphonoacetic acid and salts thereof, phosphonoformic acid and salts thereof, a 5-(2-halogenovinyl)2'-deoxyuridine, e.g. bromovinyl-deoxyuridine and acycloguanosine.

DESCRIPTION OF THE PREFERRED EMBODIMENTS

Outstanding among the combinations according to the present invention are compositions comprising G* and phosphonoacetic acid, PAA, and compositions comprising G* and phosphonoformic acid, PFA. As will be shown in the specific examples given below, in plaque reduction tests against HSV-1-Patton strain infected HFF cells, a PAA-G* combination gave in excess of 9,000 fold titre reduction, over the control experiment in the absence of any antiviral composition, whereas G* alone at thes ame dosage level gave 130 fold titre reduction, and PAA alone at the same dosage level gave a 50 fold titre reduction. In similar tests, a PFA-G* combination gave in excess of 68,000 fold titre reduction, whereas G* alone at the same dosage level gave a 24 fold titre reduction and PFF alone at the same dosage level gave a 750 fold titre reduction.

Whilst it is not intended that the present invention should in any way be limited to any specific theory as to the basis of the results obtained, the following hypothesis is offered for better and fuller understanding and explanation of the invention. Part of the explanation of the outstanding results obtainable with the combinations of the invention may, it is felt, lie in the specific modes of action by which the respective active components interfere with viral replication in the infected host cells, or the genearl metabolism of such infected host cells.

The aim of viral chemotherapy is to suppress viral replication in infected cells, or to damage the metabolism of infected cells, without substantially damaging uninfected cells. Thus, inhibition of viral replication may depend upon blocking one or more virus-specific metabolic steps in infected cells, or "poisoning" the infected cells only. The mechanism of antiviral action of acycloguanosine, for example, appear to be interaction with the herpes virus-specific thymidine kinase (TK) resulting in phosphorylation of the acycloguanosine. The resulting phosphorylated compound then inhibits the action of the herpes virus-specific DNA-polymerase (DP), thereby preventing replication of the viral DNA and replication of the virus itself. Cellular TK and DP enzymes are only slightly affected by the drug. Thus, acycloguanosine has relatively low toxicity for uninfected cells, and relatively high antiviral activity. Bromovinyl-deoxyuridine (BVDU) appears to have an essentially similar mode of action, although it may in fact only be active primarily against HSV-1 and not HSV-2. Phosphonoacetic acid (PAA) and phosphonoformic acid (PFA) appear to have only a single mechanism of action, namely interference with viral DNA polymerase, not viral thymidine kinase.

In contrast, the mode of action of G* appears to be different from that of the other drugs, and, in fact, unique. It seems that it inhibits the activity of the viral thymidine kinase enzyme, but is not involved in the activity of virus-specific DNA-polymerase. Thus the drug G* appears to be specific for viral TK and, in addition, does not require virus-specific DP for its activity. This unique anti-viral mode of action may be the reason why it is synergistic with other drugs; also, G* appears to be able to inhibit HSV mutants lacking the ability to induce DP (i.e. DP-mutants), which mutants are highly resistant to acycloguanosine, BVDU and PAA.

The preferred compositions of the present invention have been found to be extremely active against a wide representative variety of strains of HSV, both types I and II. Whilst there is some variation in the degree of activity against different HSV strains, as would be expected, there is high activity against a wide variety thereof, and synergy between the active ingredients G* and either PAA or PFA in all cases. The compositions are also similar active against equine herpesvirus of various types, and swine herpesvirus (pseudorabies virus).

Nearly every HSV strain produces virus particles which are partially resistant to each of the drugs mentioned above. For example, if one examines a typical titration curve which shows the effect of varying drug concentrations upon HSV plaque formations (the viral plaque titration method of Roizman and Roane referred to in more detail below), the curve is sigmoid, i.e. there are a few viral plaques which emerge in the presence of drug concentrations which readily suppresses other plaques. It is these partially drug-resistant virus plaques which can sometimes be suppressed by a second drug possibly having a mode of action different from the first drug. The result may be synergistic action between the first and second drugs, as set out below.

The relative amounts of the drugs in the compositions according to the invention can be varied over wide limits. The optimum amount of each drug varies according to the selection of drug, the nature of the formulation in which it is to be applied, the type and strain of HSV to be treated, and the severity and location of the infection, among other factors. In general, appropriate relative amounts will be found in the 1:200–200:1 molar range, most likely within the 25:1–1:25 molar range. The synergistic action appears to be exhibited throughou the entire range of relative proportions of the drugs. In practice, however, it is most preferred to use approximately equal proportions of the two drugs, e.g. in the 5:1–1:5 molar range.

For administration to patients, the compositions of the invention may be applied topically as ointment, cream or powder, parenterally, interthecally, as nose drops, eye drops or as an aerosol for inhalation, again depending upon the nature and location of the infection to be treated. Suitable dosage rates are in accordance with those konw and established as effective with the individual drugs of the composition. Effective unit doses for administration of the compositions interthecally or parenterally are suitably in the range from about 0.1–100 mg of each drug in the chosen combinations, per kg mammal body weight, most suitably in the 0.5–20 mg per kg and most preferably about 5 mg per kg, on the basis of a dosage administered from 2–4 times daily. It is preferred to treat the infection with relatively large doses of the combination of drugs at the outset, so as to limit the chances of development of resistant viral strains in the infection.

For optical administration, ointments or creams in conventional inert bases (e.g. petrolatum, etc.) can be formulated, in the known way. An amount from about 0.1–5 weight per cent of each drug, preferably from about 0.5–2 weight per cent of each drug, provides a suitable concentration in an ointment or cream, for topical administration 1–4 times per day. Such topically applied formulations are effectively holding a reservoir of the active drugs against the infected site, so that the concentrations of drugs in the formulations are not critical, provided of course that a dosage level harmful to surrounding skin areas it not used. With PAA, topical formulation with drug concentrations in excess of 100mM have been reported as skin irritant, whereas such amounts of PFA do not appear harmful.

DETAILED DESCRIPTION OF SPECIFIC PREFERRED EMBODIMENTS

The invention is further illustrated in the following specific experimental results and examples.

EXAMPLE 1

Human fetal fibroblasts (HFF) derived from fetal tissues were used in this study. Cells were grown and maintained in Basal Medium Eagle (BME) supplemented with 0.112% sodium bicarbonate, 2mML-glutamine, 2mg % Neomycin and 20% (vol/vol) calf serum.

A variety of HSV strains was used in the tests, as set out in the Tables presented below.

HSV-1-Patton is a well-known, standard strain, readily available from culture collections. It is known to be mid-range in terms of its sensitivity to known drugs. HSV-2-EL 1, HSV-2-EL 3, HSV-2-EL 4, HSV-2-EL 6, HSV-1-EL 11 and HSV-1-227 are recent clinical isolates.

A viral plaque titration method (Roizman and Roane, 1961) was used to deteremine the titer of the HSV strain. Tissue culture dishes (35 by 10mm, Corning)

were seeded with cells and used for assays when they were approximately 75% monolayer. Volumes (0.2ml) of logarithmic dilutions of the virus strain were inoculated onto each of two tissue culture dishes and adsorbed for 1 hr with intermittent shaking, the inoculum was removed and 2ml of 20% BME containing 0.5% human immune serum globulin was added. After a 48 hr. incubation period at 36° C. in a 5% $CO_2$ atmosphere, the overlay medium was removed, and the cell sheets were stained with a 0.05% aqueous crystal violet solution. The plaque numbers were counted with the aid of a Nikon profile projector which magnified the dishes 10X. Duplicate results were averaged, and the number of plaque-forming units (PFU) was calculated. The virus titre is thus expressed as a number of plaque forming units to be seen after growth under these conditions.

As antiviral drugs in these experiments, there were used acycloguanosine (ACG), phosphonoacetic acid (PAA), bromovinyl deoxyuridine (BVDU), phosphonoformic acid (PFA) and 9-[[2-hydroxy-1-(hydroxymethyl)ethoxy]methyl]guanine (G*). Stock solutions, 3mg/ml, of each drug were prepared as follows, kept at −20° C., and appropriate dilutions thereof were made in 20% BME just before usage:

G*—3mg dissolved in 0.1 ml distilled water and 0.9 ml 20% BME added;

ACG—3 mg dissolved in 0.1 ml of 0.1N NaOH and brought to volume with 20% BME;

PAA—3mg dissolved in 1 ml of 20% BME

PFA—3mg dissolved in 1 ml of 20% BME

BVDU—3mg dissolved in 1 ml of 20% BME.

In order to make comparisons between the activities of the various drugs and combinations, experiments were conducted by plaque titration to determine for each drug its viral ED-50 (i.e. the concentration thereof which inhibits HSV plaque formation by 50% in the HFF cells, as compared with cell cultures in the absence of the drug). For this purpose, tissue culture dishes (35 by 10 mm) with HFF cell monolayers at 75% confluence were inoculated with approximately 50 plaque-forming units of virus per 0.2 ml, and the virus was allowed to adsorb for 1 hr with intermittent shaking. After removal of the inoculum, 2 ml of 20% BME with 0.5% immune globulin and threefold dilutions of the appropriate drug were added to duplicate dishes. One set of dishes received no drug and was later used for the "no-drug control". After a 48 hr incubation period at 36° C. in a 5% $CO_2$ atmosphere, the overlay medium was removed, the cells were stained as described above, and plaques were counted. After averaging the counts of duplicate plates, the fraction of plaques emerging in the presence of each drug dilution was calculated as a percent of the control. Each drug titration was plotted on semilogarithmic graph paper, with the number of plaques per dish as vertical axis and the drug concentration as horizontal axis. The viral ED-50 concentration was that amount of drug per ml of overlay medium that inhibited plaque numbers by 50%, compared with no-drug controls, and this was read off the graphic plot of the data.

Then combinations of the drugs were tested for activity by viral plaque titration, at concentrations which were multiples of the ED-50, of the individual drugs. In combinations involving G*, BVDU and AGC, a concentration ten times that of its ED-50 was used in the combination. This was intended to ensure a concentration sufficiently high to limit the number of partially drug-resistant virus plaques to a small fraction in respect of each drug of the combination. In respect of PAA, a concentration of five times ED-50 was used, to avoid cell toxicity problems. The drugs were individually plaque titrated at the same concentrations for comparison purposes.

The results are given in Table 1 below. The figure for virus titer is expressed in plaque-forming units per ml, $\times 10^5$ and, of course, the lower the figure the greater the inhibitory, anti-viral effect of the tested drug. The figure for "Fold Titer Reduction" is the ratio of virus titer for the control, i.e. no drug, to that of the drug-present experiment.

TABLE 1 the effect of the drugs and combinations upon plaque reduction of HSV-1-Patton in HFF cells inoculated at multiplicities of infection less than one.

| DRUG | DRUG CONCENTRATION μg/ml | ED-50/ml | VIRUS TITER (PFU/ml × $10^{5)}$) | FOLD TITER Reduction |
|---|---|---|---|---|
| Control - no drug | | | 147 | 1 |
| G* | 1.2 | 10 | 1.1 | 130 |
| BVDU | 0.11 | 10 | 2.1 | 70 |
| G* + BVDU | 1.2 + 0.11 | 10 + 10 | 0.3 | 490 |
| ACG | 2.0 | 10 | 4.7 | 31 |
| G* + ACG | 1.2 + 2.0 | 10 + 10 | 0.5 | 290 |
| PAA | 250 | 5 | 3.2 | 50 |
| G* + PAA | 1.2 + 250 | 10 + 5 | 0.016 | 9,200 |
| PFA | | | | |
| G* + PFA | | • | | |

- This titration did not give a linear dose-response curve; this value was calculated from the mean plaque counts at $10^{-2-5}$ and $10^{-3}$ virus dilutions.

The results given in Table 1 shows that all of the drug combinations exhibit a degree of synergy, unpredictable from previously published details thereof. However, the G*-PAA combination is truly outstanding in its indications of activity as shown, in a totally different order of magnitude from that of either of the individual ingredients.

EXAMPLE 2

In this example, combinations of G* and phosphonoformic acid PFA were tested, by plaque titration methods, for activity against a variety of herpesvirus strains in HFF cells, using procedures previously described. A stock solution of PFA was made up ahead of time, by dissolving 3 mg PFA in 1 ml of 20% BME, and stored at −20° C. It was appropriately diluted in 20% BME just before usage. Two herpesvirus type 2 strains and one herpesvirus type 1 strain were tested. The quantities and results are set out below in Table 2:

TABLE 2

| DRUG | CONCENTRATION | VIRUS HSV-1-PATTON | | VIRUS HSV-2-EL 4 | | VIRUS HSV-2-EL 6 | |
|---|---|---|---|---|---|---|---|
| | | Virus Titer, pfu/ml × $10^5$ | Fold Titer Reduction | Virus Titer, pfu/ml × $10^5$ | Fold Titer Reduction | Virus Titer, pfu/ml × $10^5$ | Fold Titer Reduction |
| G* | 0.7 μg/ml | 140 | 24 | | | 40 | 3.8 |
| G* | 3.0 μg/ml | | | 21 | 36 | | |
| PFA | 80 μg/ml | 750 | 4.5 | 0.28 | 2,700 | 48 | 3.1 |
| G* PFA | 0.7 μg/ml 80 μg/ml | <0.05 | >68,000 | | | >0.005 | >30,000 |
| G* PFA | 3.0 μg/ml 80 μg/ml | | | 0.005 | 150,000 | | |
| No drug, control | | 3400 | 1 | 750 | 1 | 150 | 1 |

The results show that synergistic action takes place between this combination of drugs, against all three HSV strains. The apparently lower activity of G* alone against HSV-1-Patton as compared with results shown in Table 1 is probably due to a more active sample of the virus. Each strain will have different ED-50 with respect to a given drug.

EXAMPLE 3

The experiments described in Examples 1 and 2 were essentially repeated, but using the drugs G* and PAA alone and in combinations against samples of HFF cells each infected with one of six HSV strains, two of which were type 1 and four of which were type 2. Plaque titration methods as described above were used. The results are given in Table 3 below.

TABLE 3

| DRUG | CONCENTRATION µg/ml | VIRUS HSV-2-EL 1 Virus Titer pfu/ml × $10^5$ | VIRUS HSV-2-EL 1 Fold Titer Reduction | VIRUS HSV-2-EL 3 Virus Titer pfu/ml × $10^5$ | VIRUS HSV-2-EL 3 Fold Titer Reduction | VIRUS HSV-2-EL 4 Virus Titer pfu/ml × $10^5$ | VIRUS HSV-2-EL 4 Fold Titer Reduction | VIRUS HSV-2-EL 6 Virus Titer pfu/ml × $10^5$ | VIRUS HSV-2-EL 6 Fold Titer Reduction | VIRUS HSV-1-EL 11 Virus Titer pfu/ml × $10^5$ | VIRUS HSV-1-EL 11 Fold Titer Reduction | VIRUS HSV-1-227 Virus Titer pfu/ml × $10^5$ | VIRUS HSV-1-227 Fold Titer Reduction |
|---|---|---|---|---|---|---|---|---|---|---|---|---|---|
| G* | 2.0 | 8.9 | 19 | 10.0 | 7.7 | 5.9 | 130 | | | | | 0.25 | 110 |
| | 0.6 | | | | | | | 0.90 | 200 | | | | |
| | 0.4 | | | | | | | | | 0.37 | 22 | | |
| | 76 | 0.34 | 500 | | | | | | | | | | |
| | 82 | | | 0.36 | 210 | | | | | | | | |
| PAA | 90 | | | | | 0.10 | 7500 | 31.0 | 5.8 | | | | |
| | 25 | | | | | | | | | 2.8 | 2.9 | | |
| | 80 | | | | | | | | | | | 1.1 | 26 |
| | 2.0 + 76 | <0.005 | >34,000 | | | | | | | | | | |
| | 2.0 + 82 | | | <0.005 | >15,400 | | | | | | | | |
| | 2.0 + 90 | | | | | <0.005 | >150,000 | | | | | | |
| G* + PAA | 0.6 + 90 | | | | | | | <0.005 | >36,000 | | | | |
| 0.4 + 25 | | | | | | | | | <0.005 | >1,600 | | | |
| 2.0 + 80 | | | | | | | | | | | <0.005 | >930 | |
| No Drug | — | 170 | 1 | 77 | 1 | 750 | 1 | 180 | 1 | 8.0 | 1 | 28 | 1 |

These results show that synergy is exhibited between the two drugs against all of the tested HSV strains in HFF cells. The relative concentrations of the drugs in the combinations in these experiments, as in the other ecamples, are chosen on the basis of multiples of their ED-50 values as previously described. These relative amounts are appropriate for in vitro testing and to demonstrate the synergy of the combinations, but are illustrative only. Relative amounts in combinations for in vivo use and in practical administration for HSV treatments are as discussed previously, and may not bear close relationship to the proportions shown in the specific examples herein.

We claim:

1. A therapeutic composition having activity against herpes viral infections and comprising, in combiantion:
   9-[[2-hydroxy-1-(hydroxymethyl)-ethoxy]methyl[-guanine, as a first active component, and
   a second active component selected from the group consisting of phosphonoacetic acid and pharmaceutically acceptable salts thereof, phosphonoformic acid and pharmaceutically acceptable salts thereof, acycloguanosine, and a 5-(2-halogenovinyl)2'-deoxyuridine;
   said first and second active components being present in anti-virally active relative synergistic amounts from a ratio of about 1:200 to about 1:1 on a molar basis.

2. The composition of claim 1 wherein said second active component is phosphonoformic acid or a pharmaceutically acceptable salt thereof.

3. The composition of claim 2 wherein the ratio of first active component to second active component is from about 1:25 to about 1:1 on a molar basis.

4. The composition of claim 1 wherein said second active component is acycloguanosine.

5. The composition of claim 1 wherien said second active component is bromovinyl-deoxyuridine.

6. The composition of claim 1 wherein the ratio of first active component to second active component is from about 1:25 to about 1:1 on a molar basis.

7. The composition of claim 1 wherein the ratio of first active component to second active component is from about 1:5 to about 1:1 on a molar basis.

8. A therapuetic composition having activity against herpes viral infections and comprising, in combination, 9-[[2-hydroxy-1-(hydroxymethyl)-ethoxy]methyl-guanine, as a first active component, and bromovinyl-deoxyuridine as a second active component, said first and second active components being present in anti-virally active relative synetgistic amounts from a ratio of about 1:200 to about 25:1 on a molar basis.

9. The composition of claim 8 wherein the ratio of firest active component to second active component is from about 1:200 to about 14:1 on a molar basis.

10. The composition of claim 8 wherein the ratio of first active component to second active component is 14:1.

11. A therapeutic composition having activity against herpes viral infections and comprising, in combination:
   9-[[2-hydroxy-1-(hydroxymethyl)-ethoxy]methyl]guanine, as a first active component, and
   a second active component selected from the groups consisting of:
   phosphonoacetic acid and pharmaceutically acceptable salts thereof, present in an amount, with respect to said first active component, from a ratio of about 1:378 to about 1:1 on a molar basis; and
   phosphonoformic acid and pharmaceutically acceptable salts thereof, present in an amount, with respect to said first active component, from a ratio of about 1:234 to about 1:1 on a molar basis.

* * * * *